United States Patent [19]
Hildebrand et al.

[11] 4,298,395
[45] Nov. 3, 1981

[54] ACTIVATED POLYMERIC CARRIERS

[75] Inventors: Dietrich Hildebrand, Odenthal, Fed. Rep. of Germany; Thomas Gribnau, Nijmegen, Netherlands

[73] Assignee: Bayer Aktiengesellschaft, Leverkusen, Fed. Rep. of Germany

[21] Appl. No.: 962,360

[22] Filed: Nov. 20, 1978

Related U.S. Application Data

[63] Continuation of Ser. No. 792,295, Apr. 29, 1977, abandoned.

[30] Foreign Application Priority Data

May 3, 1976 [DE] Fed. Rep. of Germany ........ 2619521

[51] Int. Cl.$^3$ .................... C08L 1/02; C08L 5/12; C12N 11/06; C12N 11/10
[52] U.S. Cl. ..................... 106/163 R; 106/162; 106/205; 435/178; 435/179; 435/180; 435/181; 536/1; 536/112; 536/120; 525/375; 525/359.2
[58] Field of Search ............... 195/63; 106/205, 162, 106/163; 536/1, 51, 112, 120; 435/181, 180, 178, 179; 525/375

[56] References Cited

U.S. PATENT DOCUMENTS

| | | | |
|---|---|---|---|
| 3,542,549 | 11/1970 | Emmi | 96/111 |
| 3,619,371 | 11/1971 | Crook et al. | 536/51 |
| 3,674,767 | 7/1972 | Lilly et al. | 195/63 |
| 4,020,268 | 4/1977 | Nishikawa et al. | 536/1 |
| 4,144,128 | 3/1979 | Hilderbrand et al. | 525/375 |

FOREIGN PATENT DOCUMENTS 1125875  3/1962  Fed. Rep. of Germany .

OTHER PUBLICATIONS

Chem Abstract 57:1123e 1962.
Chem Abstract 80:61361s, 1974.

*Primary Examiner*—Allan Lieberman
*Attorney, Agent, or Firm*—Sprung, Felfe, Horn, Lynch & Kramer

[57] ABSTRACT

An activated polymeric carrier useful for bonding high and low molecular weight ligands has at least one unit thereof of the formula:

$$(T-X)_a-\underset{N}{\overset{N}{\diagup\diagdown}}-(R)_b$$

or $$(T-X)_c-\underset{N}{\overset{N}{\diagup\diagdown}}\underset{-X-T}{\overset{-(R)_d}{\diagdown}}$$

wherein
T represents atoms of the polymeric carrier;
X is a divalent oxygen or sulfur atom, —NH—, —NHR$^5$—, —CONH— or —CONR$^5$—, wherein R$^5$ is lower alkyl;
R is independently hydrogen, hydroxyl, lower alkyl, lower alkoxy, loweralkylthio, loweracylamino, nitro, cyano, carboxamide, loweralkylsulphonyl, loweralkoxycarbonyl, phenyl, trifluoromethyl or chloromethyl, provided that at least one R is halogen; and
a is 1 or 2, b is 4-a, c is 0 or 1 and d is 2-c.

10 Claims, No Drawings

ACTIVATED POLYMERIC CARRIERS

This is a continuation, of application Ser. No. 792,295, filed Apr. 29, 1977, (now abandoned).

The present invention relates to new activated polymeric carriers and a process for their preparation from polymeric carrier materials and halogenopyrimidine derivatives.

It has already been disclosed that carriers containing hydroxyl groups can be activated with cyanogen bromide and subsequently coupled with suitable effectors or ligands via free amino groups in these effectors. (R. Axen, J. Porath and S. Ernback, Nature 1967, 214, 1302–1304). However, as Tesser et al were able to show, this above mentioned process has the disadvantage that the isourea bond, which is present in this case, between the effector and the carrier is not stable to hydrolysis [G. I. Tesser et al. FEBS Letters (1972) 23, 56 and G. I. Tesser et al. Helv. Chim. Acta 57, 1718–1730 (1974)].

Another process, which goes back to E. Katchalski, Biochem. 1964, 3, 1905–1919, uses polymers containing anhydride groups. With this type of resin, the enzyme bond is due to the fact that the reaction of the amino groups of the enzyme with the anhydride groups of the resin takes place more rapidly than the competing reaction with the surrounding water.

Other processes use, for example, the reaction of epoxy groups on polymers with amino groups, thiol groups and hydroxyl groups (L. Sundberg and J. Porath, J. Chromatogr. 1974 90, 87–98), but in this case pH values of 8.5–11 and reaction times of 15 to 48 hours are required and these have a denaturing effect on numerous enzymes.

A summary of the numerous possibilities is given by, for example, C. Zaborsky in Immobilised Enzymes, CRC Press, Cleveland 1973.

Cyanuric chloride and other triazine derivatives were used by G. Kay and M. D. Lilly as early as 1967 for activating cellulose and for coupling with enzymes. (G. Kay and E. M. Crook, Nature 1967 216 514; and G. Kay, M. D. Lilly, A. K. Sharp and R. J. H. Wilson, Nature 1968 217, 641). The stability of the bond did not meet all of the requirements. Changing to the use of derivatives of trichlorotriazine (S. Kay and M. D. Lilly Biochim. Biophys. Acta (1970) 198, 276–285) resulted in better handling of the reaction but brought no improvement in the observed instability of the bonds.

The present invention now provides activated polymeric carriers having at least one unit thereof of the formula:

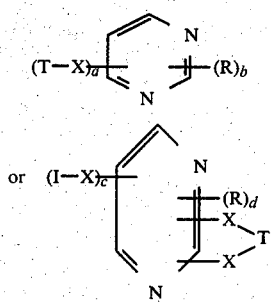

wherein
T represents atoms of the polymeric carrier;
X is a divalent oxygen or sulfur atom, —NH—, —NHR$^5$—, —CONH— or —CONR$^5$—, wherein R$^5$ is lower alkyl;
R is independently hydrogen, hydroxyl, lower alkyl, lower alkoxy, loweralkylthio, loweracylamino, nitro, cyano, carboxamide, loweralkylsulphonyl, loweralkoxycarbonyl, phenyl, trifluoromethyl or chloromethyl, provided that at least one R is halogen; and
a is 1 or 2, b is 4-a, c is 0 or 1 and d is 2-c.

The present invention also provides a method for preparing the activated polymeric carriers of the formula (I) and (II) by reacting a polymeric carrier which contains OH, SH, NH$_2$, NHR$^5$, CONH$_2$ or CONHR$^5$ groups in an organic or organic-aqueous solvent, if necessary with the addition of bases, at a temperature of between about −10° and about +30° C. with a halogenopyrimidone derivative of the formula:

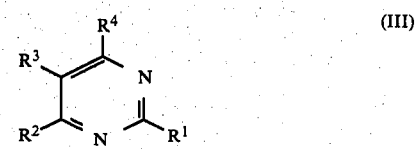

in which
R$^1$, R$^2$, R$^3$ and R$^4$ are each independently hydrogen, hydroxyl, halogen, lower alkyl, lower alkoxy, loweralkylthio, loweracylamino, nitro, cyano, carboxamido, loweralkylsulphonyl, loweralkoxycarbonyl, phenyl, trifluoromethyl or chloromethyl; provided that at least two of R$^1$ to R$^4$ are halogen.

As used herein, the terms "lower alkyl", "lower alkoxy", "loweralkylthio", "loweracylamino" and "loweralkylsulfonyl" denote radicals containing 1 to 6, preferably 1 to 4, carbon atoms, and the term "loweralkoxycarbonyl" denotes a radical containing 2 to 7, preferably 2 to 5, carbon atoms. The term "halogen" denotes fluoro, chloro, bromo and iodo.

Surprisingly, the new activated carriers of the invention possess considerably greater stability to hydrolysis than the activated carriers of related structure known hitherto. The activated carriers according to the invention, and the process for their preparation, thus represent a substantial advance in the art.

The course of the process according to the invention can be illustrated by the following greatly simplified equation:

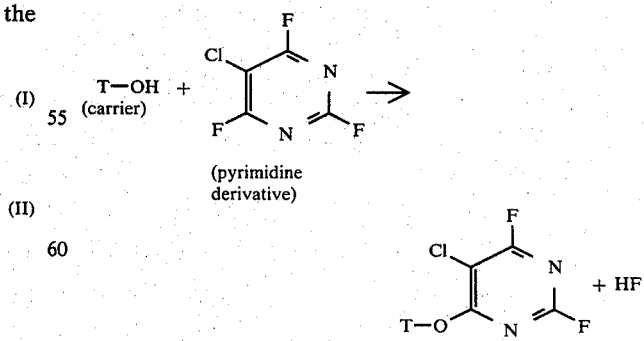

It has been assumed here, for simplicity, that in each case only one XH group (in this case X=0) of a carrier radical reacts with, in each case, one pyrimidine derivative (III). If, however, two XH groups of a carrier radical react with a pyrimidine derivative, the reaction equation can be represented, for example, as follows:

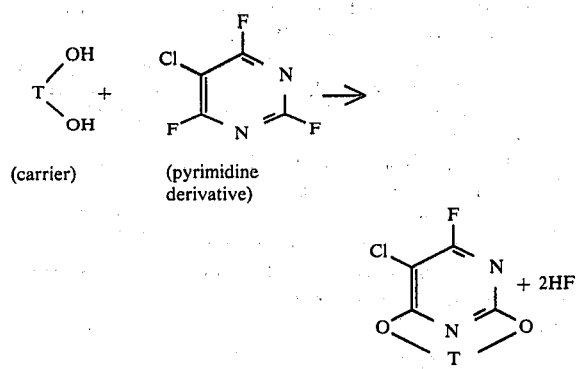

(carrier)   (pyrimidine derivative)

This mode of reaction leads to crosslinking within the polymer carrier molecule.

The polymeric carriers and halogenopyrimidone derivatives employed as starting materials in the process according to the invention are known.

Polymeric carriers which can be used for the preparation of the new activated carriers according to the invention include polymeric carrier substances, preferably carrier resins, which contain hydroxyl, $NH_2$, $NHR^5$, $CONH_2$, $CONHR^5$, or SH as functional groups. Examples which may be mentioned from the large number of possibilities are those which follow: agarose, preferably bead-shaped agarose, supplied by Pharmacia Fine Chemicals under the tradename "Sepharose", types 2 B, 4 B and 6 B, crosslinked "Sepharose" gels, types Cl-2 B, Cl-4 B and Cl-6 B, and also dextrans and crosslinked dextrans (such as, for example, "Sephadex" supplied by Pharmacia Fine Chemicals, Uppsala, Sweden, for example in types G-75, G-100, G-150 and G-200, and, furthermore, cellulose (inter alia including cotton) and various cellulose derivatives, polyacrylamide resins, ion exchanger resins containing hydrophilic groups, such as, for example, aminomethylated polystyrene resins, polyvinyl alcohols and others. In this case it is entirely possible for yet further functional groups, such as carboxymethyl groups or diethylaminoacetyl groups, also to be present. Polymers based on styrene, acrylic acid and methacrylic acid, and their esters, can also be activated if they possess at least some of the above-mentioned functional groups in their structure. Thus, for example, weakly basic anion exchangers containing primary or secondary amines can be activated. It is also possible to activate polyvinyl alcohols and polyacrylamides. In the case of polymers that initially lack the above-mentioned functional groups, these functional groups can be introduced with the aid of secondary reactions and then the groups can be activated. Thus, for example, polymers containing anhydride groups (for example ethylene/maleic acid anhydride resins) can be reacted with polyalcohols or polyamines and these can then be activated with the halogenopyrimidines. Inorganic carriers, such as porous glasses ("glass beads"), can also be reacted with compounds containing functional groups or are already available commercially, such as, for example, "Glycophase"-G from Corning. Soluble polyhydroxy compounds, such as dextran, soluble starches, polyalcohols and polyamines can also be activated with the halogenated pyrimidines.

Literature relating to some of the cited carriers: "Sepharose" from agarose: Hjerten, Biochimica, Biophysica Acta 79, 393–398 (1968) and "Sephadex" as crosslinked dextran: thesis by Per Flodin, Uppsala 1962.

The NKZ 2 and NKZ 4 ion exchanger resins which, inter alia, are used in the examples are macroporous resins of polyvinylbenzylamine and crosslinked divinylbenzene, NHZ 2 containing about 8% of divinylbenzene and NKZ 4 containing approximately 6% of divinylbenzene. Examples of other ion exchangers which can be employed according to the invention are "Amberlite" IR 45 (containing a primary amino group) and "Lewatits", for example "Lewatit" MP 600.

The following pyrimidine derivatives are particularly preferred for use in preparing the activated polymeric carrier:

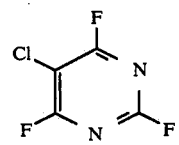

2,4,6-trifluoro-5-chloropyrimidine ("FCP")

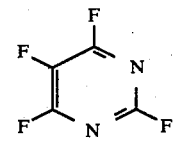

tetrafluoropyrimidine ("TFP")

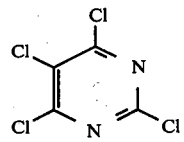

tetrachloropyrimidine ("TCP")

The preparation of FCP has been described by H. J. Schroeder et al. in J. Org. Chem. 27, 2580–2584 (1962). Other methods of preparation are to be found in the British Patent Specification 1,157,948 and British Patent No. 1,158,300.

Tetrachloropyrimidine (TCP) can be prepared easily by the method of S. J. Childress and R. L. McKee, J. Am. Chem. Soc. (1950) 72, 4271–72.

In addition to the preferred pyrimidines FCP and TCP, other pyrimidine derivatives of the general formula (III) can also be employed, such as 2-fluoro-4,5,6-trichloropyrimidine, 2,4-difluoropyrimidine, 2,4-difluoro-6-methylpyrimidine, 2,6-difluoro-4-methyl-5-chloropyrimidine, 2,4,6-trifluoropyrimidine, 2,4-difluoropyrimidine-5-ethylsulphone, 2,6-difluoro-4-chloropyrimidine, 2,4,5,6-tetrafluoropyrimidine, 2,4,6-trifluoro-5-chloropyrimidine, 2,6-difluoro-4-methyl-5-bromopyrimidine, 2,4-difluoro-5,6-dichloro- or -dibromo-pyrimidine, 4,6-difluoro-2,5-dichloro- or -dibromo-pyrimidine, 2,6-difluoro-4-bromopyrimidine, 2,4,6-trifluoro-5-bromopyrimidine, 2,4,6-trifluoro-5-chloromethylpyrimidine, 2,4,6-trifluoro-5-nitropyrimidine, 2,4,6-trifluoro-5-cyanopyrimidine, 2,4,6-trifluoropyrimidine-5-carboxylic acid alkyl esters or -5-carboxylic acid amides, 2,6-difluoro-5-methyl-4-chloropyrimidine, 2,6-difluoro-5-chloropyrimidine, 2,4,6-trifluoro-5-methylpyrimidine, 2,4,5-trifluoro-6-methylpyrimidine, 2,4-difluoro-5-nitro-6-chloropyrimidine, 2,4-difluoro-5-cyanopyrimidine, 2,4-difluoro-5-methylpyrimidine, 6-trifluoromethyl-5-chloro-2,4-difluoropyrimidine, 6-phenyl-2,4-difluoropyrimidine, 6-trifluoromethyl-2,4-difluoropyrimidine, 5-trifluoromethyl-2,4,6-trifluoropyrimidine, 5-trifluoromethyl-2,4-difluoropyrimidine and others.

When the new activated carriers of the formula (I) or (II) are prepared from polymeric carriers and pyrimidine derivatives of the formula (III), the procedure employed is such that the polymeric carrier, the halogenated pyrimidine and, if the carrier is not itself a base, also a further base for binding the hydrogen halide which is liberated, are brought together. This can be effected in an organic medium, for example dioxane, xylene or acetone or mixtures thereof, or also in organic-aqueous media. The reaction temperature is between about $-10°$ and about $+30°$ C. and preferably between about $-2°$ and about $+6°$ C.

The mixtures used by J. Warren, J. D. Reid and C. Hamalainen, Textile Res. Journal 1952, pages 584-590, for working with cyanuric chloride, and especially the xylene/dioxane system, can advantageously be used.

When tetrahalogenated pyrimidines and carriers containing hydroxyl groups are used, 1 to 2 halogens, depending on the reaction conditions, react with the carrier. Crosslinking of the carrier can thus be achieved. The effect of this is extremely advantageous in, for example, the case of agarose ("Sepharose") since, as a result, this compound becomes stable to boiling.

The choice of the halogen substituent is also decisive for the ease of reactivity. Thus, the reactivity increases from bromine via chlorine to fluorine. Moreover, the tetrahalogenated compounds are more reactive than the trihalogenated or dihalogenated compounds. Other substituents on the pyrimidine, such as, for example, lower alkoxy or loweralkylthio, may raise or lower the reactivity, such as, for example, the alkylsulphonyl group or the nitro group.

For the special case of trifluorochloropyrimidine (FCP), the following sequence has been found for the removal of the halogens by reaction:

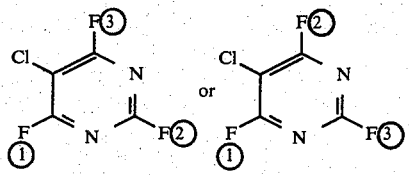

Under the conditions described below, the last halogen, that is the chlorine, does not take part in the reaction.

During activation of the carrier, the reaction can also be controlled by the amount of the alkali which is necessary for neutralization, since the reaction does not proceed at pH values below 5. The most reactive pyrimidines, such as, for example, tetrafluoropyrimidine, form a possible exception here. In the case of the other pyrimidines, it is possible, especially after removing one fluorine atom by reaction, to stop the reaction by adding acids, for example acetic acid or phosphoric acid, or a phosphate buffer of pH 5. The required alkali can be initially introduced with the carrier, for example "Sepharose", and the halogenopyrimidine can then be added and in this case, when trifluorochloropyrimidine (FCP) is used in excess alkali, two fluorine atoms first react, with the formation of crosslinking, the effect of which is, for example, that the "Sepharose" becomes stable at temperatures approaching the boiling point. If a carrier which is activated to the greatest possible degree without crosslinking is desired, either the carrier and the alkali are added together to an excess of the halogenopyrimidine or a measured amount of alkali is added to the mixture of the carrier and the halogenopyrimidine. There are no restrictions as to the choice of the base. In addition to the hydroxides of the alkali metals, it is also possible to use, for example, tertiary or quaternary ammonium compounds. The temperatures which are most advantageous for the activation depend on the reactivity of the halogenopyrimidine and on the nature of the functional group on the carrier. In the case of FCP, the reaction is advantageously carried out at temperatures of about 0° C. and with tetrachloropyrimidine, which reacts more sluggishly, the temperature used is up to room temperature and, of course, the reaction time is then also shorter. The alkylation of the hydroxyl groups generally proceeds somewhat more slowly than that of primary amino groups.

The new activated carriers prepared according to the invention can be reacted with suitable ligands to give carrier/ligand coupling products.

Most appropriately, the activated carriers are reacted with the ligand to be bonded immediately after the carrier has been activated. In many cases, however, it is possible to stabilize the activated carrier so that it is still active, and can be used, after days or even months. In the case of carriers containing hydroxyl groups, thorough washing out at low pH values, say of 5-6, suffices to keep them active for months, even in a water-moist state, at temperatures of 0°-5° C. Thus, for example, a "Sepharose" activated with FCP can be reacted with enzymes after it has been stored for 3 months without any loss in its ability to couple. In the case of carriers containing amino groups, a more rapid decline in the bonding ability has been observed under the above conditions. In many cases, drying in vacuo and storage in the dried state is then to be preferred.

Ligands which can be used for the reaction with the activated carriers are substances of low and high molecular weight, and include agents for carrying out adsorption chromatography and hydrophobic chromatography, such as, for example, hexamethylenediamine, aniline, p-aminobenzamides or ethylmercaptan, enzymes, such as, for example, trypsin, penicillinase, subtilisin, glucoseoxydase or asparaginase, other proteins, such as, for example, albumin, hormones, such as, for example, insulin, or dyestuffs, preferably azo dyestuffs, which can also be reduced with suitable reducing agents (for example sodium thionite) and reacted with suitable coupling reagents (for example also proteins).

The examples which now follow are intended to illustrate the preparation of the activated carriers according to the invention and their use for the preparation of carrier/ligand coupling products:

EXAMPLE 1

Activation of "Sepharose" with FCP 25 g of moist agarose in bead form ("Sepharose" 4 B, Pharmacia) were suspended in water and the suspension was poured into a G 3 glass suction filter, at the outlet of which an approximately 80 cm long tube, which hangs down, effects gentle suction of the water. A mark made on the filter enables a volume of 24 ml of the "Sepharose" to be filled into the filter. The "Sepharose"

was rinsed with 250 ml of distilled water. 50 ml of 3 M sodium hydroxide solution were added to the measured moist "Sepharose" and the mixture was shaken in a flask for 15 minutes at room temperature. The suspension was filtered in the same filter as above and the residue was suspended in 40 ml of a xylene/dioxane mixture (1:1, weight/weight) at 0° C. in a silicone-coated round-bottomed flask with a stirrer or vibro-mixer. A solution of 2.5 ml of trifluorochloropyrimidine (FCP, density: 1.675.) in 4 ml of the xylene/dioxane mixture is allowed to run dropwise into this suspension so slowly that the temperature does not rise above 10.5° C. One hour was required for this. After all of the FCP had been added, the reaction was stopped by adding 4.2 ml of concentrated acetic acid. The reaction mixture was poured into a suction filter and washed four times in this filter with 50 ml of the xylene/dioxane mixture and with 4 times 50 ml of dioxane and then with 1 l of distilled water. This washed, activated "Sepharose" can be stored for at least 3 months at 4° C. (see Example 13).

In contrast to untreated "Sepharose", the FCP activated "Sepharose" does not dissolve on boiling.

In order to check the activation, samples from different batches were examined by elementary analysis.

| Preparation | % N | % Cl | % F |
| --- | --- | --- | --- |
| a | 4.16 | — | — |
| b | 4.43 | — | — |
| c | 4.56 | 5.91 | 2.88 |
| d | 4.72 | 5.72 | 2.83 |
| e | 4.58 | 6.00 | 2.94 |

The following composition (-galactose-anhydrogalactose-) $(DFP_2)$ would give the analysis: 4.61% N, 5.84% Cl and 6.28% F. DFP=difluorochloropyrimidine radical. The reduced content of F can be explained by the formation of crosslinkages and by partial hydrolysis of the fluorine (54%). The residual 40% remains as reactive fluorine.

EXAMPLE 1 a

Activation of "Sepharose" with FCP 23 g of "Sepharose", which was prepared and treated with alkali according to Example 1, are added in portions to a solution, which has been cooled to 0°–3° C., of 4 g of FCP in 40 ml of a xylene/dioxane mixture (1:1 weight/weight). Forty-five minutes were required for this. The reaction was then stopped by adding 4.2 ml of concentrated acetic acid and the reaction mixture was further worked up as described in Example 1.

The elementary analysis was: 5.69% N; 5.05% F; 6.42% Cl. The following composition (-galactose-anhydrogalactose-)$_4$(DFP)$_3$ would give the analysis: 5.03% N; 6.83% F; 6.38% Cl. The somewhat reduced content of fluorine can be explained by the formation of crosslinkages and by partial hydrolysis of the fluorine (24%). The residual 76% remain as reactive fluorine.

EXAMPLE 2

Hexamethylenediamine on "Sepharose"-FCP 2 g of moist "Sepharose" activated with FCP and prepared according to Example 1 were washed with water on a glass frit and introduced into a solution of 400 mg of hexamethylenediamine (HMDA) in 20 ml of water and the suspension was mixed well. The suspension was stirred for 12 hours at room temperature. The "Sepharose" was then washed with 200 ml of water, 100 ml of 0.1 N sodium hydroxide solution, 250 ml of water and 100 ml of methanol on the glass frit and filtered and the residue was dried in vacuo to constant weight.

Analysis: 5.91, 6.95 and 7.59% N.

This corresponds to the following composition: (-galactose-anhydrogalactose-)$_3$(CP)$_2$(HMDA)~$_2$. CP=monochloropyrimidine radical.

EXAMPLE 3

Aniline on "Sepharose"-FCP 2 g of moist "Sepharose" 4 B activated with FCP and prepared according to Example 1 were washed on a glass frit with water and introduced into a solution of 50 mg of aniline in a 1:1 mixture of dioxane and McIlvain buffer of pH 7. The coupling reaction and further working up are carried out as indicated in Example 2. Analysis gave the following nitrogen content: 5.72%, 5.98% and 5.42% and this gives the following composition: (-galactose-anhydrogalactose-)$_3$(CP)$_2$(aniline)~$_2$.

EXAMPLe 4 p-Aminobenzamidine—"Sepharose" 4 B

A solution of 102 mg of p-aminobenzamidine HCl in 3 ml of a 0.1 M borate buffer of pH 7.0 and 0.5 ml of 1 N sodium hydroxide solution was added to 2.15 g of moist "Sepharose" 4 B activated with FCP and prepared according to Example 1. The suspension was stirred in a round-bottomed flask at room temperature for 20 hours. The coupling product was filtered off and washed with 200 ml of 0.1 M borate buffer of pH 7. From the determination, by spectrophotometry, of the p-aminobenzamidine in the filtrates and wash solutions and from the amount employed, it was possible to calculate a degree of substitution of 86 μmols of benzamidine per gram of moist "Sepharose".

EXAMPLE 5

Ethylmercaptan—"Sepharose" 4 B 0.1 M borate buffer of pH 9.2 and 7 ml of ethanol and 1 ml of ethylmercaptan were added to 2 g of moist "Sepharose" 4 B activated with FCP and prepared according to Example 1. The suspension was stirred for one night at room temperature. The coupling product was washed in a column with 200 ml of ethanol, 500 ml of water and 230 ml of ethanol/water (1:1, volume/volume). Elementary analysis gave a sulphur content of 2.77%. For comparison, a "Sepharose" 4 B which had not been activated but had otherwise been treated in an identical manner gave a sulphur content of less than 0.2%.

EXAMPLE 6

Albumin—"Sepharose" 4 B 3 g of moist "Sepharose" 4 B activated with FCP and prepared according to Example 1 were washed briefly with 0.1 M borate buffer of pH 9.2 and stirred in a round-bottomed flask with a solution of 400 mg of cattle serum albumin in 4 ml of a 0.1 M borate buffer of pH 9.2 for 22 hours at room temperature. The resin was filtered off, washed with the above buffer, then suspended in a 1 M ethanolamine solution of pH 9.1 and after 3 hours filtered off again and washed with buffer. All of the filtrates and wash solutions were combined and the protein content of this combined solution was determined. 280 mg were found. Accordingly, 120 mg of albumin had been bonded to the "Sepharose".

EXAMPLE 7

Albumin—"Sepharose" 4 B 800 mg of cattle serum albumin were bonded with 3 g of moist, FCP-activated "Sepharose" 4 B by the method of Example 6. The protein content of the filtrates and wash solutions was 669 mg. Accordingly, 131 mg of albumin had been bonded to the "Sepharose".

EXAMPLE 8

Insulin—"Sepharose" 4 B 3 g of moist "Sepharose" 4 B activated with FCP and prepared according to Example 1 were washed briefly with 0.1 M borate buffer of pH 9.2 and a solution of 8 P mg of insulin (cattle) in 4.5 ml of 0.1 M borate buffer of pH 9.2 was added to the washed "Sepharose" in a round-bottomed flask and the mixture was stirred at room temperature for 22 hours. The coupling product was washed with the above borate buffer and in order to complete the removal of the active halogen by-product, allowed to rotate for 17 hours at room temperature in 1 M ethanolamine of pH 9.2. After the product had again been washed with water and filtered, a degree of substitution of 8.54 mg of insulin per gram of moist "Sepharose" was obtained from the aminoacid analysis. In the lipocyte test, the formulation displayed an antilipolysis action of 85% of the theoretical activity.

The loss of bonded insulin, determined by radioimmunoassay, after 2.5 hours in Krebs solution, Ringer solution and albumin solution of pH 7.4 at 37° C. was 0.3°/00.

EXAMPLE 9

Kallikrein-trypsin inhibitor

Kallikrein-trypsin inhibitor—"Sepharose" 4 B 2.5 g of moist "Sepharose" activated with FCP and prepared according to Example 1 were suspended in 30 ml of a 0.1 M phosphate buffer of pH 7.0 and 25 mg (91 U) of kallikrein-trypsin inhibitor obtained from the lungs of cattle were added. The batch was stirred at room temperature for 20 hours. The "Sepharose"-bonded inhibitor was filtered off under a slightly reduced pressure and washed with the above phosphate buffer with and without the addition of 0.5 M sodium chloride. 2.48 g of moist "Sepharose" containing inhibitor were obtained.

The inhibitory capacity determined by the inhibition of trypsin with benzoylarginine-p-nitroanilide (BAPNA) at 25° C. of the filtrate and wash water was 27 U, and of the inhibitor on "Sepharose" was 13 U, which is 14% of the inhibitory capacity of the inhibitor employed.

EXAMPLE 10

Trypsin—"Sepharose" 4 B 2 g of "Sepharose" activated with FCP and prepared according to Example 1 were suspended at 4° C. in 30 ml of a 0.05 M phosphate buffer of pH 7.0 and 20 mg (18.6 U) of trypsin; 0.93 U/mg (as determined by BAPNA test) of trypsin were added. The mixture was stirred for 20 hours at 4° C. and then washed with 100 ml of the above phosphate buffer, which also contained 0.5 M sodium chloride, and again with 100 ml of phosphate buffer without sodium chloride. The resin was filtered off on a G 2 glass frit using a very slight vacuum. 1.59 g of moist trypsin—"Sepharose" were obtained.

The enzymatic activity (BAPNA; 25° C.) in the filtrate and in the wash buffers was less than 0.5 U, and in the enzyme resin was 6.19 U (3.9 U/g of moist weight), which is 33% of the activity employed.

EXAMPLE 11

Penicillinase—"Sepharose" 4 B-FCP 2 g of the "Sepharose" activated with FCP and prepared according to Example 1 were suspended at room temperature in 30 ml of a 0.05 M phosphate buffer of pH 7.0 and a solution of 2.5 mg of penicillinase obtained from B. cereus and having an activity of 250 U (benzylpenicillin as the substrate) was added. The batch was stirred at room temperature for 20 hours. The enzyme-resin was filtered off on a G 2 glass frit under a slight vacuum and then washed with 100 ml of the above phosphate buffer, which also contained 0.5 M sodium chloride. After a further wash with 100 ml of phosphate buffer, but without sodium chloride, the resin was filtered off again.

Yield of enzyme-resin: 1.50 g;
Enzymatic activity (benzylpenicillin; 25° C.);
Filtrate and wash water: 28 U;
Enzyme-resin: 218 U (145 U/g of moist weight).

The enzymatic activity was 87% of the activity employed or 98% of the activity of the bonded enzyme.

In order to test the stability of the bond of the enzyme to the carrier and also the enzyme activity, a 0.1 M phosphate buffer of pH 7.0 which contained 50 mg of Thimerosal per liter was allowed to flow, at a rate of 17 ml/hour, at room temperature through the enzyme-resin in a column. Samples were taken after 68 and 116 hours and their enzymatic activity was tested. After 68 hours 79% of the initial activity were found and after 116 hours 66% of the initial activity were still found. No activity could be detected in the eluates.

EXAMPLE 12

Penicillinase—"Sepharose" 4 B-FCP 3 g of moist, FCP-active "Sepharose" prepared according to Example 1, 4 ml of Palitasch borate buffer of pH 8.4 and 18.7 mg of penicillinase with an activity of 1,650 U were stirred at room temperature for 18 hours. The enzyme-resin was filtered under gentle suction and rinsed three times with 10 ml of the above buffer. In order to inactivate any FCP-activated "Sepharose" which may still be present, the resin was stirred with 10 ml of 1 M ethanolamine solution, the pH of which had been adjusted to 8.4, at room temperature for 5 hours. The resin was then transferred into a small column and rinsed with 260 ml of 1 M sodium chloride solution and with 370 ml of a 0.05% strength sodium azide solution. After removing excess wash solution under gentle suction, 4.25 g of enzyme-resin were obtained.

The enzymatic activity (benzylpenicillin, 25° C.) was 907 U (213 U/g of moist weight), which is 55% of the activity employed.

EXAMPLE 13

Penicillinase—"Sepharose" 4 B-FCP (Storage stability of activated "Sepharose")

After washing thoroughly, moist "Sepharose" 4 B activated with FCP and prepared according to Example 1 was stored for 3 months at 4° C. After this time, a 1 g sample was taken and, as described in Example 11, was reacted with 110 U of penicillinase in a buffer at pH 7 and washed. 1.71 g of moist enzyme-resin were obtained. The enzymatic activity (benzylpenicillin, 25° C.) of the filtrate and wash water was 1.8 U, and of the enzyme-resin was 101 U (59 U/g of moist weight), which is 92% of the activity employed.

EXAMPLE 14

Subtilisin—"Sepharose" 4 B-FCP 1 g of moist "Sepharose" 4 B activated with FCP and prepared according to Example 1 was suspended in 20 ml of a phosphate buffer of pH 8.0, 10 mg of substilisin (1,980 U) were added and the mixture was stirred at room temperature for 18 hours. Further working up was carried out as described for penicillinase in Example 11, and the yield was 0.91 g of the enzyme-resin. The enzymatic activity (acetyltyrosine ethyl ester, 25° C.) of the filtrate and wash water was 1,611 U and of the enzyme-resin was 272 U (299 U/g of moist weight), which is 14.1% of the enzyme activity employed or 74% of the activity of the bonded enzyme.

EXAMPLE 15

Glucoseoxydase-"Sepharose"-FCP 1 g of moist "Sepharose" 4 B activated with FCP and prepared according to Example 1 was suspended in 20 ml of a 0.1 M phosphate buffer of pH 7.0, 10 mg (1,730 U) of glucoseoxydase were added and the mixture was shaken for 18 hours at room temperature. The enzyme-resin was filtered off and washed with the above phosphate buffer, with and without the addition of 0.5 M sodium chloride, in the customary manner. Yield: 0.89 g of enzyme resin. The enzymatic activity (test with glucose and peroxydase, at 25° C.) of the filtrate and wash water was 1,290 U and of the enzyme-resin was 36 U (32 U/g of moist weight), which is 2.1% of the enzyme activity employed or 8.2% of the bonded enzyme.

EXAMPLE 16

Asparaginase—"Sepharose" 4 B 3 g of moist "Sepharose" 4 B activated with FCP and prepared according to Example 1 were added to a solution of 98.5 mg (19,400 U) of asparaginase in Palitzsch borate buffer of pH 8.4 in a round-bottomed flask and the mixture was rotated for 17 hours at room temperature. After coupling, the "Sepharose" was filtered off in a G 2 glass frit and washed 3 times with the above borate buffer. The enzyme-resin was then left to stand in 1 M ethanolamine-HCl of pH 8.4 for 5 hours at room temperature and washed in a column with 260 ml of 1 M sodium chloride solution and 370 ml of a 0.05% strength sodium chloride solution. After filtering, 5.21 g of moist enzyme-resin were obtained.

The enzymatic activity (L-asparagine, 37° C.) of the enzyme-resin was 850 U (163 U/g of moist weight), which is 4.4% of the enzyme activity employed.

EXAMPLE 17

Activation of "Sepharose" with FCP 24 g of moist "Sepharose" 4 B prepared as in Example 1 was suspended in 20 ml of xylene and 20 ml of dioxane and during this process was cooled to 0° C. 10.9 ml (32.6 mmols) of 3 N sodium hydroxide solution were added and a solution of 2.99 ml (5.0 g) (29.7 mmols) of FCP was then added in the course of 1 hour. The mixture was stirred for a further 1 hour and then worked up as described in Example 1.

Elementary analysis: 2.8% N.

EXAMPLE 18

Penicillinase—"Sepharose"-FCP 1.17 g of moist "Sepharose" 4 B activated with FCP according to Example 17 was suspended in 30 ml of a 0.05 M phosphate buffer of pH 7.0 and a solution of 2.5 mg of penicillinase (from B. cereus, 250 U) in 1 ml of the above phosphate buffer was added to this suspension. The batch was stirred at room temperature for 20 hours and worked up as described in Example 3. 1.63 g of moist enzyme-resin were obtained. The enzymatic activity (benzylpenicillin, 25° C.) of the filtrate and wash solutions was 118 U and of the enzyme-resin was 130 U, 80 U/g of moist weight, which is 52% of the activity employed or 98% of the bonded enzyme.

EXAMPLE 19

Activation of "Sepharose" with TFP

Agarose in bead form ("Sepharose" 4 B from Pharmacia) were prepared analogously to Example 1 and treated with 3 M sodium hydroxide solution. The alkaline "Sepharose", which had been subjected to suction until the original volume of 24 ml was reached, was introduced into a solution, which had been cooled to $-3°$ to 0° C., of 5.13 g of TFP (tetrafluoropyrimidine) in 40 ml of xylene/dioxane (1:1, weight/weight) in the course of about 12 minutes using an injection syringe. The batch was stirred for a total of 30 minutes and the reaction was then stopped by adding 4.5 ml of concentrated acetic acid. The activated "Sepharose" was washed, and filtered off, as described in Example 1.

Like the FCP-activated "Sepharose", the TFP-activated "Sepharose" is so strongly crosslinked that, in contrast to the starting material, it does not dissolve on boiling.

Elementary analysis 7.29% N 13.19% F.

EXAMPLE 19 a

Hexamethylenediamine on "Sepharose"-TFP 2 g of moist "Sepharose" activated with TFP according to Example 19 were stirred with 5 ml of 0.7 M hexamethylenediamine in a round-bottomed flask for 20 hours at room temperature. The product was filtered off, washed with 250 ml of water, 100 ml of 0.1 N sodium hydroxide solution and 100 ml of water and eluted in a column with a further 500 ml of water. The product was filtered off.

A deep coloration is obtained with nitrin.

For elementary analysis, the product was washed with methanol and dried in vacuo.

Analysis 6.24% F; 11.65% N.

EXAMPLE 19 b

Ethylmercaptan on "Sepharose"-TFP 2 g of moist "Sepharose" activated with TFP according to Example 19, were washed with tetrahydrofurane and added to 3 ml of tetrahydrofurane, 1 ml of triethylamine and 1 ml of ethylmercaptan. The batch was rotated in a round-bottomed flask for 17 hours at room temperature. The resin was filtered off, washed with 100 ml of ethanol and 100 ml of ethanol/water (1:1) and finally eluted in a column with 300 ml of ethanol. The product was filtered off and dried in vacuo.
Lassaigne test strongly positive
Elementary analysis: 6.51% S; 8.74% F.

EXAMPLE 19 c

Penicillinase on "Sepharose"-TFP 1 g of moist "Sepharose" 4 B activated with TFP (tetrafluoropyrimidine) according to Example 19, was suspended in 20 ml of a 0.05 M phosphate buffer of pH 7.0 and a solution of 0.5 ml (110 U) of penicillinase was added. The suspension was shaken at room temperature for 18 hours and then filtered and the product was washed with the above phosphate buffer, with and without addition of 0.5 M sodium chloride. After filtering under suction, 1.47 g of moist enzyme-resin were obtained. The enzymatic activity (benzylpenicillin, 25° C.) of the filtrate and wash solutions was 15 U and of the enzyme-resin was 79 U (54 U/g of moist weight), which is 72% of the enzyme activity employed or 85% of the activity of the bonded enzyme.

EXAMPLE 20

Activation of "Sepharose" with TCP

Agarose in bead form ("Sepharose" 4 B from Pharmacia) was prepared analogously to Example 1 and treated with 3 M sodium hydroxide solution. The alkaline "Sepharose", which had been subjected to suction until the original volume of 24 ml was reached, was introduced in portions in the course of 12 minutes at room temperature into a mixture of 4.90 g of tetrachloropyrimidine (TCP) in 40 ml of xylene/dioxane (1:1, weight/weight). During the addition, the temperature rose up to 32° C. The flask was cooled by a stream of air. The batch was stirred for a further 15 minutes. The reaction was stopped by adding 4.2 ml of concentrated acetic acid. The activated "Sepharose" was filtered off and washed with 4 times 50 ml of the dioxane/xylene mixture, with 4 times 50 ml of dioxane and with 1 liter of water and was stored in the moist form. A sample was washed with acetone and dried in vacuo. It gave the following analysis: 5.71% Cl; 2.23% N.

EXAMPLE 21

Hexamethylenediamine—"Sepharose"—TCP 10 ml of an aqueous solution of 0.35 M hexamethylenediamine were added to 1.3 g of moist "Sepharose" activated with TCP and prepared according to Example 20, in a round-bottomed flask and the mixture was stirred for 60 hours at room temperature. The product was filtered off and washed in a column with with 250 ml of water, 100 ml of 1 M sodium hydroxide solution and 250 ml of water. The substituted "Sepharose" was filtered off, washed with methanol and dried in vacuo.
Analysis: 4.67% Cl; 3.27% N.
Ninhydrin test positive.

EXAMPLE 22

Ethylenemercaptan-"Sepharose"—TCP 1.3 g of moist "Sepharose" activated with TCP and prepared according to Example 20 were washed with tetrahydrofurane, filtered off and introduced into 3 ml of tetrahydrofurane, 0.5 ml of triethylamine and 0.5 ml of ethylmercaptan. The batch was stirred in a round-bottomed flask for 60 hours at room temperature. The resin was filtered off, washed in a column with ethanol, filtered off and dried in vacuo. Lassaigne test positive.
Analysis: 4.82% Cl; 1.04% S.

EXAMPLE 23

Penicillinase—"Sepharose" 4 B—TCP 1 g of moist "Sepharose" 4 B activated with TCP (tetrachloropyrimidine) and prepared according to Example 20 was suspended in 20 ml of a 0.05 M phosphate buffer to pH 7.0 and a solution of 1 ml (110 U) of penicillinase was added. The suspension was stirred at room temperature for 18 hours and further worked up as described in Example 19 c. 1.36 g of moist enzyme-resin were obtained. The enzymatic activity (benzylpenicillin, 25° C.) of the filtrate and wash water was 9 U and of the enzyme-resin was 84 U (61 U/g of moist weight) which is 76% of the enzyme activity employed or 83% of the activity of the bonded enzyme.

EXAMPLE 24

Activation of "Sephadex" with FCP

Crosslinked dextran in bead form ("Sephadex" G 50 from Pharmacia) was activated with FCP as described in Example 1 for "Sepharose" and worked up. Elementary analysis gave a content of 0.38% of N, 0.20% of F and 0.50% of Cl.

EXAMPLE 25

Hexamethylenediamine on "Sephadex"—FCP 2 g of moist "Sephadex" activated with FCP and prepared according to Example 24 were reacted with 200 mg of hexamethylenediamine, and worked up, analogously to Example 2.
Elementary analysis: N 0.71%; F 0.10%; Cl 0.59%.

EXAMPLE 26

Ethylmercaptan on "Sephadex"—FCP 2 g of moist "Sephadex" activated with FCP and prepared according to Example 24 were reacted with a solution of 7 ml of ethanol and 1 ml ethylmercaptan, and worked up, analogously to Example 5. Elementary analysis gave a sulphur content of 0.29.

EXAMPLE 27

Penicillinase—"Sephadex" G 50

0.20 g of dried "Sephadex" G 50 activated with FCP and prepared according to Example 24 was swollen with 2 ml of water for 1 hour at 4° C. The swollen "Sephadex" was suspended in 30 ml of a 0.05 M phosphate buffer of pH 7.0 and 1 ml of a solution of penicillinase with an activity of 220 U was added. The suspension was stirred at room temperature for 20 hours. After the resin had been filtered off, it was washed with the above phosphate buffer, with and without the addition of 0.5 M sodium chloride. 1.57 g of (moist) enzyme resin were obtained. The enzymatic activity (benzylpenicillin, 25° C.) of the filtrate and wash water was 0.1 U and of the enzyme-resin was 79 U (62 U/g of moist weight), which is 44% of the activity employed.

EXAMPLE 28

Activation of cellulose with FCP 50 ml of 3 M sodium hydroxide solution were added to 4 g of cellulose (Whatman CF 11) in a round-bottomed flask and the mixture was stirred for 18 hours at room temperature. The cellulose was filtered off on a G 3 glass frit. The total amount was slowly added to a mixture of xylene and dioxane (1:1, weight/weight) which contained 7.19 g of FCP, is cooled to 0° to +5° C. and is stirred with a vibro mixer. The mixture is allowed to react for a total of 20 minutes and the reaction is then stopped by adding 5 ml of concentrated acetic acid. The activated cellulose was filtered off and washed with 4 times 50 ml of xylene/dioxane (1:1), 4 times 50 ml of dioxane and 500 ml of water and acetone. After drying in vacuo, the following elementary analysis was obtained: N: 2.43%, F: 2.43%, Cl: 2.42%.

EXAMPLE 29

Hexamethylenediamine on cellulose 5 ml of 0.35 M hexamethylenediamine in water were added to 1 g of moist cellulose activated with FCP and prepared according to Example 28. The round-bottomed flask was stirred at room temperature for 22 hours. The product was filtered off and washed with 250 ml of water, 100 ml of 1 N sodium hydroxide solution, 250 ml of water and 100 ml of acetone. The cellulose was dried in vacuo. Elementary analysis gave 3.99% of N, 0.36% of F and 2.51% of Cl.

EXAMPLE 30

Ethylmercaptan on cellulose 0.5 g of moist cellulose activated with FCP according to Example 28 was stirred with 1 ml of tetrahydrofurane, 0.5 ml of ethylmercaptan and 3 drops of triethylamine for 21 hours at room temperature. The product was filtered off, washed with 250 ml of ethanol, 50 ml of water and 50 ml of acetone and dried in vacuo.
Elementary analysis: 0.90% F; 2.35% S.

EXAMPLE 31

Trypsin—cellulose—FCP 150 g of moist cellulose (Whatman CF-11) activated with FCP and prepared according to Example 28 were suspended, at 4° C., in a solution of 50 mg (54.5 U) of trypsin in 0.01 M benzamidine-HCl phosphate buffer, according to Söüü Ä 6.0 and the suspension was mixed thoroughly for 24 hours at 4° C. in a rotating flask. After the coupling reaction, the cellulose was filtered off and washed with 50 ml of the above phosphate/benzamidine solution of pH 6. After filtering off again, the enzyme-cellulose was rotated in 5 ml of 1 M ethanolamine-HCl/0.01 M benzamidine-HCl of pH 6 for 36 hours. Filtering again and washing with 0.005 M benzamidine-HCl of pH 5.5. 1.90 g of moist trypsin-cellulose were obtained. The enzymatic activity (BAPNA, 25° C.) of the filtrate and wash solution was 26.4 U and of the trypsin-cellulose was 2.9 U (1.53 U/g of moist weight), which is 5.3% of the enzyme activity employed.

EXAMPLE 32

Penicillinase-cellulose 0.40 g of dried cellulose activated with FCP and prepared according to Example 28 was left to stand with 200 ml of water for 1 hour at 4° C. The swollen cellulose was suspended in 30 ml of a 0.05 M phosphate buffer of pH 7.0 and 1 ml of a solution of penicillinase with an activity of 220 U was added. The suspension was stirred for 20 hours at room temperature. After fitering off, the cellulose was washed with the above phosphate buffer, with and without the addition of 0.5 M sodium chloride. 0.76 g moist weight of cellulose-bonded enzyme were obtained. The enzymatic activity (benzylpenicillin, 25° C.) of the cellulose-bonded enzyme was 95 U (125 U/g of moist weight), which is 43% of the activity employed.

EXAMPLE 33

Activation of polyacrylamide with FCP 1 g of polyacrylamide in bead form (Bio-Gel P-300, 100–200 mesh wet from Bio Rad) was swollen in water for 5.5 hours and filtered off and, in a round-bottomed flask, 80 ml of 1 N sodium hydroxide solution were added and the mixture was rotated for 15 minutes at room temperature. The resin was filtered off and added in portions to a solution of 4.72 g of FCP in 40 ml of a mixture of xylene and dioxane (1:1, weight/weight). The suspension was stirred by a vibro mixer and cooled externally by a stream of air. The gel was introduced in the course of 10 minutes. During the addition, the temperature rose from 23.5° to 29° C. After a further 15 minutes the reaction was stopped by adding 3 ml of concentrated acetic acid. The resin was washed four times with 50 ml of the xylene/dioxane mixture and then with 250 ml of dioxane/water (1:1). A thick suspension of the resin in dioxane/water was poured into tetrahydrofurane, while stirring well, and the product was filtered off and washed with tetrahydrofurane. The product can be dried in vacuo.

EXAMPLE 34

Ethylmercaptan on polyacrylamide—FCP 3 ml of tetrahydrofurane, 1 ml of ethylmercaptan and 1 ml of triethylamine were added to 2.5 g of the tetrahydrofurane-moist polyacrylamide activated with FCP according to Example 33 and the mixture was stirred at room temperature for 14 hours. The resin was filtered off, washed with ethanol and further extracted, in a column, with 250 ml of ethanol. The washed product was filtered and dried in vacuo. Lassaigne test positive.
Elementary analysis: 0.44% of sulphur

EXAMPLE 35

Penicillinase on polyacrylamide—FCP 100 mg of dry polyacrylamide activated with FCP according to Example 33 were suspended in 20 ml of a 0.05 M phosphate buffer of pH 7.0 and 0.5 ml of a solution of penicillinase (110 U) was added. The suspension was shaken overnight at room temperature. The enzyme resin was filtered off and washed with the above phosphate buffer, with and without the addition of 0.5 M sodium chloride. 2.59 g of moist enzyme-resin were obtained. The enzymatic activity (benzylpenicillin, 25° C.) of the filtrate and wash solutions was 85 U and of the enzymeresin was 22.4 U (8.6 U/g of moist weight), which is 20% of the enzyme activity employed or 90% of the bonded enzyme.

EXAMPLE 36

Activation of ion exchangers with FCP 20 g of a weakly basic, macroporous ion exchanger based on polystyrene and containing primary amino groups (NKZ-4), which have been washed with methanol and water, were suspended in 150 ml of a 0.05 M phosphate buffer of pH 6 and the pH was adjusted to 6 with a little 1 N hydrochloric acid. A solution of 2 ml of FCP in 20 ml of dioxane is allowed to run in dropwise in the course of 1 hour, while stirring, at room temperature. During the addition, the pH value was kept constant at pH 6 by adding 0.1 N sodium hydroxide solution. Subsequently, the resin was stirred for a further 30 minutes, then filtered off and washed with a solution of 0.1 M acetic acid, 0.5 M sodium chloride and water. Yield: 2.2 g of resin. It is best to use the FCP-activated resin immediately thereafter for the coupling reaction. On storage in the moist state at 4° C., the ability for enzyme coupling decreases by about 10% per day.

EXAMPLE 37

Penicillinase on NKZ-4-FCP 2 g of moist polystyrene resin (NKZ 4-FCP) activated with FCP and prepared according to Example 36 were suspended in 40 ml of a 0.05 M phosphate buffer of pH 7.0, and a solution of 5 mg (440 U) of penicillinase was added. The reaction mixture was stirred at room temperature for 28 hours. The resin was filtered off and worked up as described in Example 35. 2.33 g of enzyme-resin were obtained. The enzymatic activity (benzylpenicillin, 25° C.) of the enzyme resin was 180 U (77 U/g of moist weight), which is 41% of the enzyme activity employed.

EXAMPLE 38

Activation of ion exchangers with FCP

Aminomethylated polystryene resin (NKZ-2) was dried for 2 days at 40° C. and then for 2 days under a high vacuum at room temperature. 10 g of dry resin were added, at 0.5° C., to a solution of 10 g of FCP in 50 ml of toluene. The resin was suspended using a vibro mixer and 5.5 ml of triethylamine were added dropwise. After a total of 1 hour, the reaction was stopped by adding 3 ml of concentrated acetic acid. The resin was filtered off, washed five times with 50 ml of toluene and five times with 50 ml of diethyl ether, filtered off and dried in vacuo. The dry resin is stored in a refrigerator.

EXAMPLE 39

Ethylmercaptan on aminomethylated polystyrene—FCP 3 ml of tetrahydrofurane, 1.5 ml of ethylmercaptan and 1.6 ml of triethylamine were added to 2 g of dry, aminomethylated polystyrene resin (NKZ-2) activated with FCP according to Example 38 and the mixture was rotated for 28 hours at room temperature. The resin was filtered off and washed with ethanol and diethyl ether and dried in vacuo.

Elementary analysis: 0.44% of sulphur.

EXAMPLE 40

Penicillinase on NKZ-2-FCP 3 g of dried polystyrene resin (NKZ-2-FCP) activated with FCP and prepared according to Example 38 were suspended in 25 ml of Sörensen phosphate buffer of pH 7.0 and a solution of 10 mg (880 U) of penicillinase was added. The reaction mixture was shaken at room temperature for 28 hours. The resin was filtered off, washed with the above buffer and, in order to remove the reactive halogen, shaken in 25 ml of a 1 N ethanolamine solution of pH 8.0 for a further 1 hour at room temperature. The resin was filtered off and washed in the customary manner with phosphate buffer, with and without the addition of 0.5 M sodium chloride. 6.4 g of enzyme-resin were obtained. The enzymatic activity (benzylpenicillin, 25° C.) of the filtrate and wash solutions was 13 U and of the enzyme-resin was 163 U (25.5 U/g of moist weight), which is 18.5% of the enzyme activity employed.

What is claimed is:

1. An activated polymeric carrier having at least one unit thereof of the formula:

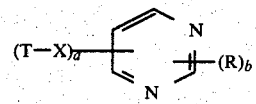

or 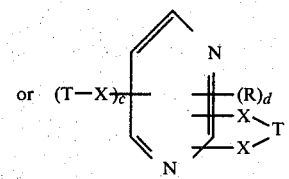

wherein

T represents atoms of the polymeric carrier selected from the group consisting of agarose, crosslinked dextran, cellulose, polyacrylamide and aminoethylated polystyrene resin;

X is a divalent oxygen or sulfur atom, —NH—, —NHR$^5$—, —CONH— or —CONR$^5$—, wherein R$^5$ is lower alkyl;

R is independently hydrogen, hydroxyl, lower alkyl, lower alkoxy, loweralkylthio, loweracylamino, nitro, cyano, carboxamide, loweralkylsulphonyl, loweralkoxycarbonyl, phenyl, trifluoromethyl or chloromethyl, provided that at least one R is halogen; and a is 1 or 2, b is 4-a, c is 0 or 1 and d is 2-c.

2. The activated polymeric carrier according to claim 1, in which the carrier is agarose.

3. The activated polymeric carrier according to claim 1, wherein each R is halogen.

4. The activated polymeric carrier according to claim 1, which is agarose activated by 2,4,6-trifluoro-5-chloropyrimidine.

5. A process for the production of the activated polymeric carrier of claim 1, in which a polymeric carrier containing at least one OH, —SH, —NH$_2$, —NHR$^5$ lower alkyl, —CONH$_2$ or —CONHR$^5$, in which R$^5$ is lower alkyl, is reacted in an organic or organic-aqueous solvent, at a temperature of between about −10° and about +30° C., with a halogenopyrimidine of the formula:

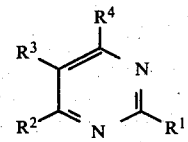

in which each of R$^1$, R$^2$, R$^3$ and R$^4$ is independently hydrogen, halogen, hydroxyl, lower alkyl, lower alkoxy, loweralkylthio, loweracylamino, nitro, cyano, carboxamido, loweralkylsulphonyl, loweralkoxycarbonyl, phenyl, trifluoromethyl or chloromethyl, provided at at least two of R$^1$ to R$^4$ is halogen.

6. The process according to claim 5, in which the polymeric carrier is selected from the group consisting of agarose, crosslinked dextran, cellulose, polyacrylamide and aminomethylated polystryene resin.

7. The process according to claim 5, wherein each of $R^1$ to $R^4$ is halogen.

8. The process according to claim 7, in which the halogenopyrimidine is 2,4,6-trifluoro-5-chloropyrimidine, tetrafluoropyrimidine or tetrachloropyrimidine.

9. The process according to claim 5, in which the carrier is agarose and the halogenopyrimidine is 2,4,6-trifluoro-5-chloropyrimidine.

10. The process according to claim 5, in which a base is present during the reaction.

* * * * *

UNITED STATES PATENT AND TRADEMARK OFFICE
CERTIFICATE OF CORRECTION

PATENT NO. : 4,298,395
DATED : November 3, 1981
INVENTOR(S) : Dietrich Hildebrand, et al It is certified that error appears in the above-identified patent and that said Letters Patent is hereby corrected as shown below:

Col. 1, line 60    Delete "$(1-X)_c$" and insert --$(T-X)_3$--

Col. 4, line 8    Delete "NHZ" and insert --NKZ--

Col. 7, line 12    Delete "10.5°" and insert --+0.5°--

Col. 15, line 43    Delete "Söuü A" and insert --Sörensen, of pH--

Signed and Sealed this

Nineteenth Day of July 1983

[SEAL]

Attest:

GERALD J. MOSSINGHOFF

*Attesting Officer*    *Commissioner of Patents and Trademarks*